United States Patent [19]

Goldman et al.

[11] Patent Number: 4,737,582

[45] Date of Patent: Apr. 12, 1988

[54] ABSORBENT VEGETABLE MATERIALS

[75] Inventors: Stephen A. Goldman; David V. Myhre; Herbert L. Retzsch, all of Cincinnati, Ohio

[73] Assignee: The Procter & Gamble Company, Cincinnati, Ohio

[21] Appl. No.: 750,567

[22] Filed: Jun. 28, 1985

[51] Int. Cl.$^4$ .................. C08B 37/06; C08L 5/06; A61F 13/16; A61F 13/20

[52] U.S. Cl. ........................ 536/2; 106/162; 428/411.1; 428/221; 428/532; 604/364; 604/368; 604/904

[58] Field of Search ............. 536/2; 428/411.1, 221, 428/532; 106/162; 604/904, 364, 368

[56] References Cited

U.S. PATENT DOCUMENTS

| | | | |
|---|---|---|---|
| 2,147,521 | 2/1939 | Bustamante | 426/549 |
| 2,215,944 | 9/1940 | Vincent | 426/431 |
| 2,362,014 | 11/1944 | Lissauer et al. | 426/254 |
| 3,903,889 | 9/1975 | Torr | 604/365 |
| 3,982,003 | 9/1976 | Mitchell et al. | 426/1 |
| 4,009,313 | 2/1977 | Crawford et al. | 428/290 |
| 4,143,172 | 3/1979 | Mitchell et al. | 426/532 |
| 4,174,417 | 11/1979 | Rydell | 428/221 |
| 4,225,628 | 9/1980 | Lynn | 426/549 |
| 4,256,111 | 3/1981 | Lassen | 604/368 |
| 4,292,972 | 10/1981 | Pawelchak et al. | 604/368 |
| 4,333,461 | 6/1982 | Muller | 604/368 |
| 4,341,207 | 7/1982 | Steer et al. | 128/155 |
| 4,360,021 | 11/1982 | Stima | 604/365 |
| 4,379,782 | 4/1983 | Staub et al. | 514/54 |
| 4,461,890 | 7/1984 | Manabe et al. | 536/2 |
| 4,468,428 | 8/1984 | Early et al. | 428/221 |
| 4,596,567 | 6/1986 | Iskra | 604/368 |

FOREIGN PATENT DOCUMENTS

| | | |
|---|---|---|
| 57-54573 | 4/1982 | Japan . |
| 1207352 | 9/1970 | United Kingdom . |
| 1555647 | 11/1979 | United Kingdom . |

*Primary Examiner*—Ronald W. Griffin
*Attorney, Agent, or Firm*—Jerry J. Yetter; Kim W. Zerby; George W. Allen

[57] ABSTRACT

This invention provides novel, highly absorbent pectin-containing vegetable materials, and a process for making these materials by incorporating into pectin-containing vegetable materials substituents which contain cation exchange groups. The present invention further provides absorbent structures containing these materials, as well as disposable absorbent procuts containing the materials or absorbent structures of the present invention.

58 Claims, No Drawings

ABSORBENT VEGETABLE MATERIALS

TECHNICAL FIELD

This invention relates to novel absorbent materials of vegetable origin, the process for making such absorbent materials, absorbent structures containing these materials, and disposable absorbent products containing these materials and absorbent structures.

BACKGROUND OF THE INVENTION

Disposable absorbent products (e.g. disposable diapers, sanitary napkins, and the like) generally contain absorbent webs of wood pulp fibers. Depending on the climate, it takes a tree from about twenty years to about forty years to mature to a harvestable state. Consequently, in order to meet the demands for wood pulp fibers to be used in absorbent materials, vast areas of land are necessary for the growing of trees. As another consequence, even though wood pulp fibers are probably the most economical materials used in disposable absorbent products available today, substantial expenditures are made in harvesting and growing of the trees. There is, therefore, a continuing need for alternative, inexpensive, absorbent materials, preferably from renewable resources.

It has now been discovered that certain pectin-containing agricultural byproducts can be converted to highly absorbent materials, suitable for use in disposable absorbent products, via a relatively simple and inexpensive process. Typical examples of agricultural by-products suitable as raw materials for the absorbent materials of the present invention include the residue materials from citrus juice processes and from sugar beet refineries. These materials are abundantly available at low cost. Pectin-containing agricultural residue material can be converted to a highly absorbent material by introducing into the materials sufficient anionic groups as to obtain a cation exchange capacity of from about 0.5 meq/g to about 6 meq/g of the vegetable material. The vegetable-derived absorbent materials typically have an absorbent capacity which is from two to five times that of conventional wood fiber webs. These materials, therefore, offer an opportunity to reduce the bulk of absorbent products while maintaining their containment capacity.

It is, therefore, the object of this invention to provide an inexpensive, absorbent material suitable for use in disposable absorbent products. It is another object of this invention to provide a process for converting certain pectin-containing agricultural waste materials to the absorbent materials of this invention.

It is a further object of this invention to provide absorbent structures which comprise, in addition to a conventional absorbent material, the novel absorbent material of the present invention. It is also an object of the present invention to provide disposable absorbent products, like disposable diapers and sanitary napkins, comprising the absorbent vegetable materials and absorbent structures of the present invention.

BACKGROUND ART

The agricultural waste materials suitable as starting materials for the manufacture of the absorbent materials of the present invention are being produced in large quantities. The citrus pulp waste material from citrus juice processors, consisting of peels (i.e. albedo and flavedo) and rag, is generally processed to cattle feed by what has been termed the "lime de-watering process". This process comprises the steps of treating the waste with "lime" (calcium oxide, calcium hydroxide, or even calcium carbonate) to convert it from a slimy, unpressable condition to a watery, pressable condition; pressing the converted waste; and drying (see, for example, U.S. Pat. No. 2,147,521, issued Feb. 14, 1939 to Bustamante; U.S. Pat. No. 2,215,944, issued Sept. 24, 1943 to Vincente, U.S. Pat. No. 2,362,014, issued Nov. 7, 1944 to Lissauer et al.).

Relatively small quantities of citrus waste are used as a source of pectin, which can be used as a thickening agent in food products. Food thickening agents may also be prepared by comminuting citrus peel materials, and lowering the degree of esterification of the pectic materials in the citrus peel by enzymatic or chemical treatment. This approach has been disclosed in U.S. Pat. No. 3,982,003 issued Sept. 21, 1976 to Mitchell et al., and in U.S. Pat. No. 4,143,172, issued Mar. 6, 1979 to Mitchell et al. Another attempt at converting citrus waste to a food additive for human consumption is disclosed in U.S. Pat. No. 4,225,628, issued Sept. 30, 1980 to Lynn. According to the process described in this reference, citrus peel particles are de-watered by a process very similar to the lime de-watering process used in cattle feed production; the material is subsequently mixed with sesame grain flour, ground, dried and milled to a desired particle size. U.S. Pat. No. 4,379,782, issued Apr. 12, 1983 to Staub et al. discloses the use of citrus albedo or sugar beet pulp as a dietary fiber. The materials are extracted with water or isopropanol to remove soluble carbohydrates and color and flavor materials. In spite of these attempts at finding more profitable uses for citrus waste, almost all of the citrus waste from juice canneries is still being converted to cattle feed and sold at a price which barely provides for recovery of the processing costs.

Sugar beet residue (commonly referred to as beet pulp), like citrus residue, is generally converted to cattle feed. As for citrus residues, attempts have been reported to convert beet pulp into a food additive suitable for human consumption. An example is Japanese Patent No. SHO 57-54573, publication date Apr. 1, 1982. This patent discloses a method for upgrading beet pulp by bleaching the pulp in hypochloric acid at pH 6.5 to 7.5, washing with water and drying. The material is reported to be capable of absorbing about 90% of its weight in water. British Specification No. 1,555,647 discloses a process for converting sugar beet chips to food additives of improved color involving the step of bleaching with hydrogen peroxide in an aqueous alkaline suspension. The alkaline material disclosed for use in this process is calcium hydroxide.

U.S. Pat. No. 4,386,580, issued June 7, 1983 to Johnson, discloses the use of dried ground citrus pulp or sugar beet pulp as an animal litter material. U.S. Pat. No. 4,292,972, issued Oct. 6, 1981 to Pawelchak et al., discloses a foam article used as a surgical sponge. The sponge material contains hydrocolloid, gelatin, pectin, and sodium carboxymethylcellulose.

European Patent Application Publication No. 137,611, by Rich, published Apr. 17, 1985, discloses pectin-containing absorbent vegetable materials and a process for preparing them involving deesterification of the pectin to less than about 45%. European Patent Application Publication No. 137,608 by Rich, published Apr. 17, 1985, discloses absorbent structures which contain the pectin-containing absorbent vegetable materials above.

SUMMARY OF THE INVENTION

The present invention relates to a vegetable material comprising: (1) from about 5% to about 60% pectin; (2) from about 5% to about 60% of substituents containing cation exchange groups which have been incorporated into the vegetable material; (3) from about 0.5 meq/g to about 6.0 meq/g of cation exchange groups; and (4) from about 20% to about 85% of non-pectin vegetable material.

This invention further relates to a process for producing absorbent vegetable materials having from about 0.5 meq/g to about 6 meq/g of cation exchange groups, starting with vegetable materials containing from about 15% to about 60% pectin, comprising: (1) performing the steps, one or more times in any order, of (a) incorporating into the vegetable material substituents containing cation exchange groups to the extent of from about 0.5 meq to about 6.0 meq of cation exchange groups per gram of substituent-containing vegetable material; and (b) optionally, modifying the vegetable material to increase its cation exchange capacity; and (2) adjusting the pH of the vegetable material to the desired pH using a base or acid containing an exchangeable cation.

The invention also relates to absorbent structures comprising: (1) from about 1% to about 99% of absorbent vegetable material of the present invention in its salt form; and (2) from about 1% to about 99% of a conventional absorbent material.

The invention further relates to disposable absorbent products, such as diapers or sanitary napkins, comprising the absorbent structures of the present invention. Such absorbent products typically comprise (a) a liquid impervious backing sheet; (b) a hydrophobic top sheet; and (c) an absorbent structure according to the present invention, said structure being placed between the backing sheet and the top sheet.

DETAILED DESCRIPTION OF THE INVENTION

This invention is based upon the discovery that pectin-containing vegetable material can be converted into absorbent materials using a relatively simple and inexpensive process. This process involves the addition of cation exchange groups to the components of a high pectin content vegetable material.

In general, the process for producing absorbent vegetable materials having from about 0.5 meq/g to about 6 meq/g of cation exchange groups, starting with vegetable materials containing from about 15% to about 60% pectin, comprises:
(1) performing the steps, one or more times, in any order, of
   (a) incorporating, into the vegetable material, substituents containing cation exchange groups to the extent of from about 0.5 meq to about 6.0 meq of cation exchange groups per gram of substituent-containing vegetable material; and,
   (b) optionally, modifying the vegetable material to increase its cation exchange capacity; and
(2) adjusting the pH of the vegetable material to the desired pH using a base or acid containing an exchangeable cation.

By "exchangeable cations" as used herein is meant cations which can readily be exchanged from the vegetable absorbent material under conditions as normally occur during the absorption of body fluid like urine or menses, i.e., a temperature of about 100° F. (37° C.) or below, and a pH in the range of from about 5 to about 8. Suitable exchangeable cations include alkali metal cations, in particular sodium and potassium, ammonium and tetraalkylammonium, (e.g., tetramethylammonium, tetraethylammonium, etc.), and protons. These cations are bound to the cation exchange groups of the vegetable material.

By "cation exchange groups" as used herein is meant anionic groups bound to exchangeable cations. The term includes strong acid functional groups, like sulfonate, sulfate, phosphonate, phosphate, and arsonate groups as well as weak acid groups like carboxylic, phosphoric and phenolic groups. Preferred cation exchange groups are phosphate and carboxylate. By "cation exchange capacity" as used herein is meant the milliequivalents of cation exchange groups per gram of vegetable material.

Pectin-containing vegetable materials which are suitable as starting materials for the process disclosed in the present invention contain at least about 15%, but not more than about 60%, pectin. Preferred starting materials have from about 20% to about 50% pectin. The non-pectin component of the vegetable material may consist of cellulose, hemicellulose, lignin, chloroform-soluble lipids, non-lipid organic materials (extractable with chloroform, methanol, water in volume ratio of 20:4:1), and other materials commonly found in pectin-containing vegetable material. Typically, the major portion of the non-pectin fraction of the vegetable material is cellulose, hemicellulose, lignin or a mixture thereof.

Examples of suitable vegetable materials include apples, apricots, citrus pulp, sugar beets, and watermelon rinds. Zucchini, for example, which has a pectin content of about 8%, is not suitable. It is also possible to use a mixture of the suitable vegetable materials, e.g., a mixture of from about 1% to about 99% of sugar beet pulp and from about 1% to about 99% citrus pulp.

Citrus pulp and sugar beet pulp, each of which is a byproduct of an important agricultural industry, are available in large quantities and at low cost, and therefore are preferred starting materials for the preparation of the absorbent materials of the present invention. Sugar beet pulp is the most preferred.

One example of a suitable starting material for the process of the present invention is the vegetable-derived material generated in European Patent Application Publication No. 137,611 by Rich, published Apr. 17, 1985, and European Patent Application Publication No. 137,608, by Rich, published Apr. 17, 1985, the disclosures of both of which are incorporated herein by reference. This material is pectin-containing vegetable material which has been partially deesterified.

The amount of pectin in the vegetable starting material may be calculated from the total amount of bound metals and the methoxy content of the vegetable starting material. The bound metal content is determined by first extracting the vegetable starting material with chloroform, followed by a 40 hour Soxhlet extraction with chloroform/methanol/water (20/4/1, v/v/v), and then dry ashing followed by flame atomic absorption analysis for the calcium, magnesium, sodium and potassium remaining in the vegetable material after the extraction (i.e., metals which cannot be removed by chloroform extraction or chloroform/methanol/water extraction). The methoxy content is determined by base hydrolysis followed by GC analysis for the liberated methanol.

The underlying assumptions for this analysis for pectin are that pectin does not contain any free acid groups, that all of the pectin is anhydrogalacturonic acid, and that no insoluble alkaline earth metal salts, other than calcium salts, are present. These assumptions have been verified by independent methods to be correct within a reasonable margin of confidence.

The pectin content of the vegetable starting material may also be determined by the colorimetric determination of hexuronic acids as disclosed in Wardi et al., *Anal. Biochem.*, 57, 268 (1974), the disclosures of which are incorporated herein by reference.

The process of the present invention for making vegetable absorbent materials involves the derivatization of the above described pectin-containing vegetable starting material. The key element of the derivatization process is the incorporation into the vegetable material, at some point in the process, of substituents containing cation exchange groups. The incorporation of these substituents into the vegetable material is done to the extent that from about 0.5 meq to about 6.0 meq of cation exchange groups per gram of substituent-containing vegetable material are added to the vegetable material.

The incorporation of substituents containing cation exchange groups involves more than commingling material which contains cation exchange groups with the vegetable material to give a mixture. In general, it involves a chemical addition of substituents containing cation exchange groups into the vegetable material, probably by reaction with hydroxyl groups contained therein. Reactions of this type are well known from cellulose chemistry. For example, carboxyl groups may be introduced by reacting sodium chloroacetate with the hydroxyl groups. In this way, carboxymethyl groups are incorporated into the vegetable material through ether linkages. The preferred method is to react the vegetable material with polyprotic acid, or the anhydride or acid halides (preferred being acid chlorides) of such acids. For example, phosphate groups may be incorporated into the vegetable material by reaction with phosphorus oxychloride or polyphosphoric acid. Also as an example, succinate or maleate groups may be incorporated into the vegetable material by reaction with succinic anhydride or maleic anhydride.

By "polyprotic acids", as used herein, is meant an acid capable of dissociating two or more protons. Specific examples include phosphoric acid, sulfuric acid and organic dicarboxylic acid. Preferred dicarboxylic acids include succinic acid, maleic acid and orthophthalic acid, as well as substitution products containing such groups as alkyloxic, halogen, nitro, and hydroxyyl. The anhydrides of the dicarboxylic acids are more reactive and are preferred for use herein. Succinic anhydride and maleic anhydride, which incorporate the preferred substituents succinate and maleate into the vegetable material, are particularly preferred. Also preferred is phosphorus oxychloride and polyphosphoric acid which incorporate the preferred substituent phosphate into the vegetable material.

The reactions of most acid anhydrides or acid halides with the vegetable material to incorporate these substituents must be carried out in a non-aqueous solvent. Moreover, usually a base must be present to catalyze the reaction and to neutralize the acid formed. Thus, good results are obtained by using pyridine as the solvent for the reaction. However, surprisingly good results can also be obtained by using acetone as a solvent and triethylamine as a catalyst for the reaction. This method avoids the use of the highly toxic and expensive pyridine and thus is preferred for use herein. Other trialkylamines may be used as the catalyst, e.g., tributylamine, and other non-aqueous solvents may be used in place of the acetone, e.g., dimethylformamide or acetonitrile.

Not all of the cation exchange groups contained in the vegetable materials produced by the process of the present invention need be the result of incorporating substituents containing cation exchange groups into the vegetable material. The process may optionally include (either before and/or after incorporating substituents containing cation exchange groups) a step (or steps) in which the vegetable material itself is modified to increase the cation exchange capacity of the material. This may be done, for example, by partially deesterifying the pectin in the vegetable material, by exchanging the calcium and magnesium in the material with exchangeable cations or by converting hydroxyl groups into carboxyl groups (e.g., by oxidation with nitrogen dioxide).

In its natural state typically about 60% of the pectin is present as the methyl ester. By alkaline treatment at pH 8-11 the degree of esterification is reduced. The degree of esterification for citrus pulp may be reduced to as low as about 5%. However, it is preferred that the degree of esterification should not be reduced to less than about 30% since the pectin tends to be come solubilized when excessive deesterification occurs. If deesterification of the vegetable material is included in the process of the present invention, deesterification with base is preferred, but other methods of deesterification may be used such as enzymatic or acid catalyzed processes. Base deesterification of pectin-containing vegetable materials is disclosed in European Patent Application Publication No. 137,611, by Rich, published Apr. 17, 1985, the disclosures of which are incorporated herein by reference.

The pectin-containing vegetable materials also naturally contain significant amounts of calcium and magnesium ions associated with carboxyl groups of the pectin. These cations are not "exchangeable" in the meaning as defined herein. It has been discovered that divalent metal pectates, in particular calcium pectates, are far inferior to pectates containing exchangeable cations with regard to absorbent properties. This is probably due to the fact that divalent metal salts of pectin are "cross-linked", whereby the divalent metal ion serves as the link between two adjacent pectin molecules. This cross-linking is believed to prevent swelling of the pectin and to thereby reduce its absorbent capacity. Non-limiting examples of ways to remove the calcium and magnesium are as follows. The calcium and magnesium can be replaced with sodium by soaking the material in a 1M NaCl aqueous solution at neutral pH, and subsequently washing the material with a 1M NaCl solution and then water. The calcium and magnesium can also be replaced by treating the pectin-containing material with a 1M HCl solution in a 60/40 ethanol/water mixture for a few minutes (preferred being from about 1 to about 10 minutes), and then washing.

The process of the present invention is controlled (over the step(s) of incorporating substituents containing cation exchange groups and the step(s), if performed, of modifying the vegetable material to increase the cation exchange capacity of the material) to give a vegetable material which has from about 0.5 meq/g to about 6.0 meq/g of cation exchange groups. Preferred is from about 1.0 meq/g to about 3.5 meq/g, and most preferred is from about 1.5 meq/g to about 2.5 meq/g.

The final step of the process of the present invention involves adjusting the pH of the vegetable material to the desired pH. The desired pH of the vegetable material depends on the use to be made of the material. If it is to be used solely to influence the pH of an absorbent structure, for example to give an acidic or basic diaper, then the desired pH may be any pH that produces the pH sought for that structure. However, the vegetable materials of the present invention have been found to have excellent "supersorber-like" absorbent properties when the vegetable material is in its salt form at pH of from about 5 to about 10, preferably being pH from about 6 to about 8.5, and it is this material which is preferred for use in the absorbent structures of the present invention. Thus, as used hereinafter, the term "salt form" means the vegetable material of the present invention which has a pH of from about 5 to about 10. In addition, the highly protonated vegetable material of the present invention is useful as a fibrous cation exchange material. Thus, as used hereinafter, the term "acid form" means the vegetable material of the present invention which has a pH below about 5. Adjusting the pH of the vegetable material may be done using a base or acid which contains an exchangeable cation, e.g., NaOH, KOH, or HCl. The vegetable material as obtained from the process described hereinabove is generally in particulate or fibrous form.

The vegetable materials of the present invention are comprised of: (1) from about 5% to about 60% pectin; (2) from about 5% to about 60% of substituents containing cation exchange groups which have been incorporated into the vegetable material; (3) from about 0.5 meq/g to about 6 meq/g of cation exchange groups (all or part of which are attributable to the incorporated substituents containing cation exchange groups), with from about 1.0 meq/g to about 3.5 meq/g preferred, and from about 1.5 meq/g to about 2.5 meq/g most preferred; and (4) from about 20% to about 85% of non-pectin vegetable material.

The non-pectin portion of the material is predominantly the non-soluble polymeric materials commonly found in pectin-containing vegetable materials, e.g., cellulose, hemicellulose, and/or lignin. Other minor constituents of the non-pectin portion may be chloroform-soluble lipids and/or non-lipid organic materials extractable with a mixture of chloroform, methanol and water (chloroform:methanol:water in volume ratio of 20:4:1). More specifically, as a non-limiting example, the non-pectin portion of the vegetable material may consist of: (1) from about 80% to about 100% of a material selected from the group consisting of cellulose, hemicellulose, lignin, and mixtures thereof; (2) from about 0% to about 5% chloroform-soluble lipids; and (3) from about 0% to about 15% non-lipid organic materials extractable with a mixture of chloroform, methanol and water (chloroform:methanol:water in volume ratio of 20:4:1).

Analysis of the vegetable materials in the present invention may be done in the following way. The pectin content can be determined by the colorometric determination of hexuronic acids as disclosed in Wardi, et al., *Anal. Biochem.*, 57, 268 (1974), the disclosures of which are incorporated herein by reference.

The percentage of certain substituents (e.g., succinate, maleate) containing cation exchange groups which have been incorporated into the vegetable material may be determined by gas chromatography ("G.C.") following liberation of the substituent from the vegetable material (e.g., by hydrolysis), and, if necessary, derivatization of the substituent for G.C. analysis. For example, the amount of incorporated succinate is determined using the following procedure. The succinylated vegetable material is hydrolyzed in trifluoroacetic acid (containing an internal standard such as adipic acid) at 120° C. for 24 hours to free the incorporated succinate. An aliquot is taken and evaporated to dryness. The residue, which contains the succinic acid and internal standard, is derivatized in pyridine with BSTFA (N,O-bis-trimethylsilyl-trifluoroacetamide) using standard procedures. Gas chromatography is used to analyze the derivatized residue and determine the quantity of succinate in the starting material. Determination of phosphate substituents may be achieved by dry ashing followed by phosphomolybdate analysis for free phosphate. Other substituents containing cation exchange groups may be analyzed by methods well known to those skilled in the art.

The cation exchange capacity of a material may be determined by titrating the acid form with aqueous NaOH. For example, 0.05 gram of the vegetable material is dispersed in 100 ml of 1N NaCl. The suspension is hydrated for one hour. In order to facilitate the titration, the particle size is then reduced using two minutes of high-speed mechanical disruption in a blender. The suspension is then titrated to pH=7.5 using a standardized solution of NaOH. The same procedure is followed for a blank solution. The difference in volume of titrant required is used to calculate the meq/g of cation exchange groups in the vegetable material.

The absorbent structures of the present invention comprise (1) from about 1% to about 99% of the vegetable material of the present invention, with the salt form preferred, and (2) from about 1% to about 99% of a conventional absorbent material. Methods for making absorbent structures are disclosed in European Patent Application Publication No. 137,698, by Rich, published Apr. 17, 1985, the disclosure of which is incorporated herein by reference.

By "conventional absorbent material" as used herein is meant any absorbent material, or mixture of absorbent materials, which is being used, or has been proposed for use, in absorbent products like disposable diapers, sanitary napkins, disposable towels, facial tissues, toilet tissues, incontinent pads, bandages, and the like. Examples thereof include absorbent fibers, water-insoluble hydrogels and mixtures of absorbent fibers and water-insoluble hydrogels. Examples of absorbent fibers include vegetable fibers like cotton fibers, wood pulp fibers (e.g., Kraft pulp fibers, chemo-thermo mechanical pulp filters), and fibers of abaca, sisal, henequen, cantala, istle, mauritirus, phornium, sansevieria, caroa, plassava, broomroot, flax, hemp, ramie, jute, kenaf, roselle, urena, coir and kapok. Examples of conventional absorbent materials further include man-made fibers like rayon, cellulose acetate, cellulose triacetate, alginate fibers, protein fibers, polyamide, nylon-6,6, nylon-6, aromatic polyamides, polyester, acrylic fibers, polyethylene and polypropylene fibers. Many of the man-made fibers are hydrophobic, but can be hydrophilized using art-disclosed techniques. Hydrophobic fibers may be hydrophilized by surfactant treatment, as disclosed in U.S. Pat. No. 3,916,447, issued Nov. 4, 1975, to Thompson; and in U.S. Pat. No. 4,100,324, issued July 11, 1978 to Anderson et al., the disclosures of which are incorporated herein by reference. Thermoplastic fibers may further be hydrophilized by coating with a hydrophilic material, e.g. silica, or by surface-grafting the fibers with hydrophilic groups. Absorbent materials comprising silica film coatings are disclosed in U.S. Pat. No. 4,469,746, issued Sept. 4, 1984 to Weisman et al., the disclosures of which are incorporated herein by reference.

By "hydrogel" as used herein is meant an inorganic or organic compound capable of absorbing aqueous fluids and retaining them under moderate pressures. For good results, the hydrogels must be water insoluble. Examples are inorganic materials such as silica gels and organic compounds such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in U.S. Pat. No. 3,901,236, issued to Assarsson et al., Aug. 26, 1975, the disclosures of which are incorporated herein by reference. Particularly preferred polymers for use herein are hydrolyzed acrylonitrile grafted starch, acrylic acid grafted starch, polyacrylates, and isobutylene maleic anhydride copolymers, or mixtures thereof.

Processes for preparing hydrogels are disclosed in U.S. Pat. No. 4,076,663, issued Feb. 28, 1978 to Masuda et al; in U.S. Pat. No. 4,268,082, issued Aug. 25, 1981 to Tsubakimoto et al.; and further in U.S. Pat. Nos. 3,734,876, 3,661,815, 3,670,731, 3,664,343, 3,783,871, and Belgian Pat. No. 785,858; the disclosures of all of which are incorporated herein by reference.

Preferred for use herein is an absorbent structure comprising a vegetable material of the present invention in its salt form and a conventional absorbent material which is cellulose fibers, in particular wood pulp fibers. In a preferred embodiment the absorbent structure comprises from about 5% to about 80% vegetable material of the present invention in its salt form, and from about 20% to about 95% wood pulp fiber.

The vegetable material of the present invention in its salt form and the conventional absorbent material can be combined in a variety of ways to form the absorbent structures of the present invention. For example, vegetable material of the present invention in its salt form can be mixed with conventional absorbent fibers and the mixture formed into a web; or particulate vegetable material of the present invention in its salt form can be introduced into a web of conventional absorbent fibers in a certain pattern, so as to create areas of increased absorbent capacity within the absorbent structure; or the vegetable material of the present invention in its salt form can be pressed into a sheet which is then placed against a web, or sandwiched inbetween webs of the conventional absorbent fibers. Other executions will be apparent to those skilled in the art.

The absorbent structures may conveniently be made by using conventional equipment designed for air laying of hydrophilic fibrous webs. In such equipment, webs are typically formed by taking up hydrophilic fibers in an air flow and depositing the fibers on a wire mesh screen. By metering the desired quantities of vegetable material particles or fiber particles of the present invention into the air flow at a point just upstream of the wire mesh screen, the desired mixture of hydrophilic fibers and vegetable material particles of the present invention can be made. The web formed on the screen is then passed through calender rolls which are set to a nip pressure resulting in the desired density of the absorbent structure. It will be clear that this embodiment of the process requires only minor modifications of conventional equipment for the manufacture of absorbent structures, i.e., installing a metering device for the addition of the vegetable material particles or fibers of the present invention. In certain instances it may be necessary to replace the standard wire mesh screen on the equipment with one of a finer mesh size. This need will arise when relatively small particles are used, and/or when the mesh size of the standard screen is relatively coarse.

Optionally, the structures may be compressed to a higher density than that of conventional air-laid wood pulp fiber webs (i.e., a density higher than about 0.1 $g/cm^3$) by increasing the nip pressure on the calender rolls. The densified absorbent structures have good absorbent properties, in spite of the reduced void volume of such structures, and better wet strength and dry strength than non-densified structures. This is due to the wet resiliency exhibited by the material. It regains virtually all of its original volume if wetted in a densified state and therefore exhibits its high absorbency in both an uncompressed and compressed state (unlike wood pulp fiber webs which become distinctly less absorbent upon compression). The densified structures therefore have properties (low bulk, high absorbency) which are highly desirable for absorbent products like disposable diapers, incontinent pads and sanitary napkins. The densified structures have a density of from about 0.1 $g/cm^3$ to about 1 $g/cm^3$, preferably from about 0.15 to about 0.5 $g/cm^3$. Densified absorbent structures are disclosed in U.S. Pat. No. 4,610,678, issued Sept. 9, 1986 to Weisman et al. the disclosures of which are incorporated herein by reference.

Alternatively, an absorbent structure may be formed by placing a web of absorbent fibers against a sheet of vegetable material of the present invention in its salt form. Optionally, the sheet and/or the web may be wrapped in envelope tissue, to increase the lateral strength of the structure.

Alternatively, an absorbent structure can be formed by mixing absorbent fibers, e.g., wood pulp fibers, and particles of the vegetable material of the present invention in its salt form in an aqueous slurry; admixing a surfactant; and foaming with air. The foamed slurry is then conveyed onto a wire screen and dewatered, preferably by applying vacuum to the underside of the wire screen. The foamed mat thus obtained is subsequently dried in air. The material can be put into sheet form by applying pressure to wet-laid material, and subsequent drying. A more detailed description of the foaming process is disclosed in U.S. Pat. No. 3,871,952, issued Mar. 18, 1975 to Robertson, the disclosures of which are incorporated herein by reference.

The absorbent structures of the present invention encompass structures comprising the vegetable material of the present invention in its salt form and a water-insoluble hydrogel. Examples include structures comprising a mixture of hydrogel particles or fibers and particles or fibers of the vegetable material of the present invention in its salt form; and laminates comprising one or more sheets of hydrogel material and one or more sheets of vegetable material of the present invention in its salt form, e.g. a laminate of one sheet of water-insoluble hydrogel placed against a sheet of vegetable material of the present invention, or a "sandwich" type laminate, comprising a sheet of water-insoluble hydrogel material placed in between two sheets of vegetable material of the present invention in its salt form. Many variations are possible, as will be apparent to those skilled in the art. As above, the mixture can be densified to a density of about 1 g/cm$^3$ without significant loss of absorption capacity, preferably having a density of from about 0.15 g/cm$^3$ to about 0.5 g/cm$^3$.

A preferred embodiment is an absorbent structure comprising a mixture of from about 50% to about 95% vegetable material of the present invention in its salt form and from about 5% to about 50% of a water-insoluble hydrogel. Both the hydrogel and the vegetable absorbent material in its salt form are preferably in particulate or fibrous form.

Excellent absorbent structures are also obtained upon mixing of (1) hydrophilic fibers (e.g. cellulose fibers), (2) particles or fibers of the vegetable material of the present invention in its salt form, and (3) particles or fibers of a water-insoluble hydrogel. The three components can be mixed in any ratio. Preferred are structures comprising from about 30% to about 80% hydrophilic fibers; from about 10% to about 50% vegetable material of the present invention in its salt form; and from about 5% to about 50% water-insoluble hydrogel. More preferred are structures comprising from about 40% to about 70% hydrophilic fibers; from about 20% to about 40% vegetable material of the present invention in its salt form; and from about 5% to about 25% water-insoluble hydrogel.

The performance of these three-component structures is improved by densifying the structures to a density of from about 0.1 to about 1 g/cm$^3$, preferably from about 0.15 to about 0.5 g/cm$^3$.

In addition, the absorbent structures of the present invention can contain other components appropriate for the properties desired of the structure (e.g., wet strength additives, binders, etc.). For example, to improve the strength of the absorbent structures of the present invention, the structures can be mixed with a small amount (typically from about 0.5% to about 5%) of a long thermoplastic fiber. As used herein, long fiber means a fiber having a length of more than about 1 inch (about 2.5 cm). Suitable thermoplastic materials are inexpensive polymers like polyethylene, polypropylene and polyester. Polyester fibers are preferred because they are more hydrophilic than polyolefin fibers. The use of thermoplastic fibers in absorbent structures for the purpose of improving the strength of such structures is described in more detail in U.S. Pat. No. 4,307,721, issued Dec. 29, 1981 to Tsuchiya et al.,; U.S. Pat. No. 4,219,024, issued Aug. 26, 1980 to Patience et al.; and in U.S. Pat. No. 4,100,329, issued July 11, 1978 to Anderson et al.; the disclosures of all of which are incorporated herein by reference. Other additives will be apparent to those skilled in the art.

Because of their particular properties, the absorbent structures of this invention are extremely suitable for use in disposable absorbent products. By "disposable absorbent product" herein is meant a consumer product which is capable of absorbing significant quantities of water and other fluids, like body fluids. Examples of disposable absorbent products include disposable diapers, sanitary napkins, incontinent pads, paper towels, facial tissues, bandages, and the like. The absorbent structures of the present invention are particularly suitable for use in products like diapers, incontinent pads, bandages, and sanitary napkins. It is possible to design absorbent products which are thin and yet have more than sufficient absorbent capacity to avoid the embarrassment and inconvenience of failure. Flexibility of the structure ensures comfort for the wearer and a good fit of the absorbent product.

Disposable diapers comprising the absorbent structures of the present invention may be made by using conventional diaper making techniques, but replacing the wood pulp fiber web core which is typically used in conventional diapers with an absorbent structure of the present invention. Articles in the form of disposable diapers are fully described in Duncan and Baker, U.S. Pat. No. Re. 26,151, issued Jan. 31, 1967; Duncan, U.S. Pat. No. 3,592,194, issued July 13, 1971; Duncan and Gellert, U.S. Pat. No. 3,489,148, issued Jan. 13, 1970; Buell, U.S. Pat. No. 3,860,003, issued Jan. 14, 1975; and Duncan, U.S. Pat. No. 3,952,745, issued Apr. 27, 1976; which patents are all incorporated herein by reference. A preferred disposable diaper for the purpose of this invention comprises an absorbent core containing an absorbent structure of the present invention; a topsheet superposed or co-extensive with one face of the core; and a liquid impervious backsheet superposed or co-extensive with the face of the core opposite the face covered by the topsheet. The diaper may further comprise a second absorbent core, like a wood pulp fiber web, or a sheet of water-insoluble hydrogel. The backsheet most preferably has a width greater than that of the core thereby providing side marginal portions of the backsheet which extend beyond the core. The diaper is preferably constructed in an hourglass configuration.

The backing sheet (or backsheet) of the disposable absorbent products herein can be constructed, for example, from a thin, plastic film of polyethylene, polypropylene, or other flexible moisture impeding material which is substantially water impervious. Polyethylene, having an embossed caliper of approximately 1.5 mils, is especially preferred.

The topsheet of the disposable absorbent products herein can be made in part or completely of synthetic fibers such as polyester, polyolefin, rayon, or the like, or of natural fibers such as cotton. The fibers are typically bound together by a thermal binding procedure or by a polymeric binder such as polyacrylate. This sheet is substantially porous and permits a fluid to readily pass therethrough into the underlying absorbent core. The topsheet can be made more or less hydrophobic depending upon the choice and treatment of fiber and binder used in the construction thereof. The topsheets used in the articles of the present invention are relatively hydrophobic in comparison with the abosrbent core of said articles. Topsheet construction is generally disclosed in Davidson, U.S. Pat. No. 2,905,176, issued Sept. 22, 1959; Del guercio, U.S. Pat. No. 3,063,452, issued Nov. 13, 1962; and Holliday, U.S. Pat. No. 3,113,570, issued Dec. 10, 1963, which patents are incorporated herein by reference. Preferred topsheets are constructed from polyester, rayon, rayon/polyester blends or polypropylene.

The salt form of the vegetable material of the present invention is preferred for use in absorbent structures to be used in disposable diapers because of the supersorber-like characteristic of this material. Because of its significantly greater absorbency over conventional absorbent materials, replacement on a weight-by-weight basis by the salt form of the vegetable material of the present invention for conventional absorbent material results in a reduction in volume and a gain in capacity for a diaper of equal weight. The replacement may be on a less than equal weight basis, thereby sacrificing part of the gain in absorbent capacity in favor of an even greater reduction in bulk. Substitution of conventional absorbent material is also desirable for producing a densified diaper which is highly absorbent yet has less bulk. The salt form of the vegetable material of the present invention can be densified without the loss of absorbent capacity observed when conventional absorbent material is densified. Further, diapers containing the salt form of the vegetable absorbent material of the present invention appear to have a lower failue rate (based on the percent of diapers that leak a given amount of fluid at a particular volume of fluid added to the diaper) compared to diapers made of conventional absorbent material. Finally, use of the salt form of the vegetable material of the present invention may be preferred over hydrogel. Hydrogel loses much of its absorbent capacity when the fluid has a high salt content, a phenomenon called "salt poisoning". The salt form of the absorbent material of the present invention is not salt poisoned.

Because the absorbent structures of the present invention are highly absorbent, and yet thin and flexible, they are extremely suitable for use in sanitary napkins. As is the case with disposable diapers, sanitary napkins utilizing the present absorbent structures may be derived from conventional sanitary napkins by simply replacing the absorbent core thereof (typically a web of wood pulp fibers) with an absorbent structure of the present invention. Such replacement may be on a weight-by-weight basis, which results in a reduction in volume and a gain in capacity; or the replacement may be on a less than equal weight basis, thereby sacrificing part of the gain in absorbent capacity in favor of an even greater reduction in bulk. Further reduction in bulk is possible by utilizing densified absorbent structures of the present invention.

An example of a sanitary napkin comprises a pad of the absorbent structure of the present invention; a hydrophobic topsheet; and a fluid impervious bottom sheet. The topsheet and the backsheet are placed at opposite sides of the absorbent structure. Optionally, the absorbent structure is wrapped in envelope tissue. Suitable materials for top sheets, bottom sheet and envelope tissue are described more fully above and are well known in the art. A more detailed description of sanitary napkins and suitable materials for use therein is found in U.S. Pat. No. 3,871,378, issued Mar. 18, 1975 to Duncan et al., the disclosures of which are incorporated herein by reference.

Use of the salt form of the vegetable material of the present invention is preferred for use in sanitary napkins for the same reasons given for use in a diaper. However, of particular importance for use in sanitary napkins is the insensitivity of the material to salt poisoning, unlike hydrogel material. Another possible performance advantage that the salt form of the vegetable material of the present invention has over hydrogel materials is its greater ability to absorb macro-molecules/particles, which are present in menses, into its capillary structure. Comparison of the absorbent capacity for menses of wood pulp (southern softwood kraft), a hydrogel material (Sanwet IM-1000, a starch acrylate material marketed by Sanyo Chemical Industries, Inc.), and the salt form of a vegetable material of the present invention (the material produced in Example 15 below) is made in Table 1. The procedure for obtaining the data in Table 1, and the composition of the synthetic (water-based) menses and artificial (blood-based) menses, are given hereinbelow.

TABLE 1

| | Modified Rewet Test Capacity Data | |
|---|---|---|
| | X-Load (g/g)[1] | |
| Absorbent Material | Synthetic Menses | Artificial Menses |
| Wood Pulp | 13.0 | 16.0 |
| Sanwet IM-1000 | 23.1 | 15.0 |
| Example 15 material | 20.0 | 20.7 |

[1]X-load = weight of fluid absorbed (in grams) per gram of absorbent material.

The material of the present invention is clearly superior at absorbing artificial menses (a blood based solution), being about 40% better than hydrogel and about 20% better than conventional absorbent material. It is to be noted that while hydrogel performs substantially poorer for artificial (blood based) menses than synthetic (water based) menses, the material of the present invention performs nearly the same for both.

Modified Rewet Test

The Modified Rewet Test entails wetting 0.050 gms of the absorbent material being tested with synthetic (water-based) menses or artificial (blood-based) menses. After swelling, the absorbent material is placed under a 0.25 psi confining weight for 5 minutes. The liquid holding capacity results, which are tabulated in Table 1 above, are reported as the X-load values, which is the weight (in grams) of the menses absorbed per gram of absorbent material being tested.

The synthetic menses to be utilized for the test is prepared as follows. Place a 10 gallon stainless steel tank equipped with a Lightnin stirrer and a dial thermometer on a hot plate. Add 24,640 ml ± 50 ml distilled water to the tank. Add 280 ± 0.5 g of NaCl and 112 ± 0.5 g $Na_2CO_3$ to the distilled water, mixing vigorously until solution is achieved. Heat the solution to 80 ± 5° C. with the tank covered to minimize evaporative loss. Resume stirring prior to addition of a mixture of 2220 ± 5 ml of glycerol (99%) and 129.0 ± 0.5 g of carboxymethylcellulose (7MF Grade). The resulting solution has physical characteristics which permit its use in absorbency tests to anticipate the performance of an absorbent material for human menses.

The artificial menses to be utilized for this test is prepared as follows. The artificial menses is made up of a "mucus component" and a blood component. The mucus component's ingredients are 3.1 g gastric mucin (ICN; 6.2%); 0.2 ml of an 8.5-9.5% aqueous lactic acid solution, to be prepared from a 1:10 dilution of 85-95% lactic acid (USP, Baker); 0.75 ml of a 10% aqueous KOH solution; and 46.0 ml phosphate buffered saline (pH=7.2) to be prepared by mixing 280 ml of solution A (1.38 g $NaH_2PO_4$ in 1 mole $H_2O$ and 8.5 g NaCl diluted with $H_2O$ to 1 liter) and 720 ml of solution B (1.42 g $Na_2HPO_4$ and 8.5 g NaCl diluted with $H_2O$ to 1 liter). The mucus component is prepared by mixing the above ingredients, heating over medium low heat for approxmately 30 minutes while stirring at medium speed, autoclaving at 121° C. for 10–15 minutes, and then cooling. The artificial menses is prepared by swirling to mix the above prepared mucus component with the blood component, which is 50 ml of sterile defibrinated sheep blood (Cleveland Scientific). This artificial menses very closely simulates human menses for absorbency tests.

Equilibrium Sorption Test

The absorption properties of absorbent materials are determined by their absorption behavior with "synthetic urine" (a solution of 1% NaCl, 0.06% $MgCl_2.H_2O$ and 0.03% $CaCl_2.H_2O$ in distilled water, the surface tension of the solution being adjusted to 45 dynes/cm with about 0.0025% of an octylphenoxy polyethoxy ethanol surfactant (Triton X-100, from Rohm and Haas Co.)) and distilled water. The basic procedure is described by Burgeni and Kapur, "Capillary Sorption Equilibria in Fiber Masses", *Textile Research Journal*, 37, 362 (1967), which publication is incorporated herein by reference.

The absorption apparatus consists of a liquid reservoir connected by glass tubing, a valve, and tygon tubing to a glass funnel containing an ASTM 4-8 micron frit on which the absorbent sample is placed. The liquid reservoir, which has a capacity of approximately 50 mls and is covered to minimize evaporation, is positioned on the pan of an electronic balance. Liquid that is absorbed by the sample is drawn out of the reservoir through a fine-tip glass tube. This tube passes through a small hole in the cover of the reservoir without contacting either the cover or the bottom of the reservoir. The glass frit funnel is mounted on a vertical pole. The height of the frit above the liquid level in the reservoir determines the hydrostatic suction being exerted on the sample. This can be varied from 0–100 cm. Absorption is initiated by opening the valve between the frit and the reservoir. The weight of liquid absorbed by the sample is determined by the change in weight of the liquid in the reservoir.

In a typical experiment, the frit is positioned at 0 cm with the valve to the reservoir in the off position. A layer of absorbent material having a diameter of six centimeters is positioned on the frit. Two cylindrical confining weights having diameters of six centimeters and weights of approximately 200 gms and 1800 gms are placed on top of the absorbent material. Together, these weights extert a confining pressure of 1.0 psi. Absorption is first measured under the 1.0 psi confining pressure for a period of twenty minutes. The heavier weight is then removed and the additional absorption, in twenty minutes, under the residual confining pressure of 0.1 psi is measured. This absorption is added to the initial absorption to give the total weight of liquid absorbed under the 0.1 psi confining pressure.

The absorption capacity of the absorbent material for each confining weight is defined as the amount of fluid (in grams) absorbed per gram of absorbent material at 0 cm hydrostatic pressure.

EXAMPLE 1

Synthesis of Absorbent Vegetable Material from Sugar Beet Pulp by Succinylation (a) Raw Materials Sugar beet pulp is obtained directly from a sugar beet processing plant. The pulp is diverted from the processing stream prior to pulp drying. The moisture content of the pulp as received is 75%. 64 grams of this never-dried sugar beet pulp is dispersed in deionized water (1% solids) and shredded in a blender for one minute to reduce particle size. The resulting pulp dispersion is filtered, redispersed in deionized water, and adjusted to pH 7.5 by addition of 1N NaOH. The pulp dispersion is then filtered and the solids resuspended in water (1% solids) and refiltered to remove water-soluble components. Water is removed from the insoluble fraction by exchange with ethanol, followed by exchange with acetone, followed by drying under vacuum. 13.5 grams of solid material is obtained corresponding to a dry-weight yield of 84%.

The pulp obtained after this washing and drying is 26.9% by weight pectin, with a degree of esterification of 57%, as determined by analysis for bound metals and methoxy content (Table 2). The pectin anhydrogalacturonate that is not esterified is mostly present as the calcium and magnesium salts. Less than 10 mole % of the pectin anhydrogalacturonate groups are present as monovalent-cation salts.

TABLE 2

| Component | Percent of Dry Weight | Meq/g | Mole % |
|---|---|---|---|
| Calcium | 0.46 | 0.23 | 16 |
| Magnesium | 0.33 | 0.27 | 19 |
| Sodium | 0.15 | 0.07 | 5 |
| Potassium | 0.14 | 0.04 | 3 |
| Methoxy ($CH_3O$) | 2.52 | 0.81 | 57 |
| Pectin | 26.9 | | |

The absorbency of the washed and dried pulp for synthetic urine, as measured by the equilibrium-sorption test, is 6.6 g/g and 12.0 g/g for confining weights of 1.0 psi and 0.1 psi, respectively (Table 3). The absorbency of the washed and dried pulp for distilled water, as measured by the equilibrium-sorption test, is 7.5 g/g and 14.2 g/g for confining weights of 1.0 psi and 0.1 psi, respectively.

TABLE 3

| Example # | Sugar-Beet Materials | Absorption of Synthetic Urine (g/g) | |
|---|---|---|---|
| | | 1.0 psi | 0.1 psi |
| 1a | Sugar Beet Pulp | 6.6 | 12.0 |
| 1c | Na-Salt Form of Succinylated Pulp | 11.9 | 18.8 |
| 2b | Na-Salt Form; Ca/Mg-Free Succinylated Pulp | 12.5 | 20.2 |

(b) Succinylation of Sugar Beet Pulp with Succinic Anhydride in Pyridine 4.0 grams of the washed and dried pulp is dispersed in 800 mls pyridine (0.5% solids) in a 3-neck one liter round-bottom flask. The dispersion is stirred under a blanket of nitrogen gas for 30 minutes. To this dispersion is added 6.0 grams of succinic anhydride. The dispersion is stirred at ambient temperature for 10 minutes to dissolve the succinic anhydride. Stirring is continued as the dispersion is heated to 80° C. After two hours at this temperature, the slurry is cooled to room temperature and filtered. The solids are redispersed 2× in ethanol and 2× in acetone to remove pyridine and unreacted succinic anhydride. The acetone is removed by room temperature drying in a vacuum oven. 5.5 grams of dried succinate-substituted sugar beet material is obtained, corresponding to a dry weight increase of 36%.

The cation exchange capacity of this substituent-containing (i.e., succinylated) sugar beet material, is measured by titration, is 3.4 meq/g.

(c) Conversion of Succinylated Sugar Beet Pulp to Sodium-Salt Form.

1.0 gram of the succinylated sugar beet pulp from part (b) above is dispersed in 100 ml of deionized water. The pH of the dispersion is adjusted to pH 8.5 with 1N NaOH and then maintained at this pH for one hour using a Radiometer recording titration system and pH stat. The dispersion is then filtered, the solids redispersed in water, and the water removed as described in part (b) above. 1.04 grams of dried product is obtained, corresponding to a weight increase of 4%. The cation exchange capacity is not substantially affected by this procedure.

The absorbency of the product, which has a cation exchange capacity of 3.3 meq/g, for synthetic urine is measured using the equilibrium-sorption test. The absorption capacity is 11.9 g/g and 18.8 g/g for confining weights of 1.0 psi and 0.1 psi, respectively (Table 3). This represents an increase in absorption capacity relative to the unreacted sugar beet pulp of 80% and 57%, respectively. Liquid sorption is very rapid with an uptake under the 1 psi confining weight of more than 10 g/g in the first minute.

EXAMPLE 2

Synthesis of Absorbent Vegetable Material from Sugar Beet Pulp (a) Conversion of Succinylated Sugar Beet Pulp to its Ca/Mg-Free Form 2.5 grams of the succinylated sugar beet pulp of Example 1 (b) is dispersed in approximately 200 ml of EtOH/H$_2$O (60/40 V/V). The dispersion is stirred for approximately 45 minutes followed by the addition of 5 ml of concentrated HCl. After 3 minutes of stirring, the dispersion is filtered. The filter cake is resuspended 2× in EtOH/H$_2$O (60/40 V/V). Water is removed using the procedure of Example 1. 2.4 grams of dried product is obtained.

The cation exchange capacity of the product, as measured by titration, is 3.6 meq/g.

(b) Conversion of Ca/Mg-Free Succinylated Sugar Beet Pulp to Sodium-Salt Form 1.0 gram of the vegetable material from part (a) is converted to the sodium-salt form using the procedure described in Example 1(c). 1.06 grams of dry product is obtained, corresponding to a weight increase of 6%. The cation-exchange capacity is not substantially affected by this procedure. Flame atomic absorption analysis of the product shows that calcium and magnesium levels are substantially reduced compared to the unreacted pulp as well as the succinylated pulp of Example 1(c), where acid treatment is not used.

The absorbency of the product, which has a cation exchange capacity of 3.4 meq/g, for synthetic urine is measured using the equilibrium-sorption test. The absorption capacity is 12.5 g/g and 20.2 g/g for confining weights of 1.0 psi and 0.1 psi, respectively (Table 3). Liquid sorption is very rapid with an uptake under the 1 psi confining weight of more than 10 g/g in the first minute.

EXAMPLE 3

Variations on Example 1

The succinylation procedure described in Example 1(b) is followed except for varying the weight ratio of added succinic anhydride to washed and dried sugar-beet pulp, the weight:volume ratio of pulp:pyridine, and the reaction time. The % weight change resulting from each reaction and the cation exchange capacity of the dried product, as measured by titration, are given in Table 4.

TABLE 4

| Product Code # | Pulp (g) | Pyridine (ml) | Succinic Anhydride (g) | Reaction Time (Hrs) | % Wt. Change | Cation Exchange Capacity (meq/g) |
|---|---|---|---|---|---|---|
| 3A | 1.0 | 90 | 0.0 | 4.0 | −1 | 0.0 |
| 3B | 1.0 | 150 | 0.4 | 0.5 | +11 | 1.0 |
| 3C | 1.0 | 150 | 1.0 | 0.5 | +16 | 1.6 |
| 3D | 1.0 | 150 | 1.0 | 2.0 | +29 | 2.7 |
| 3E | 4.0 | 200 | 8.0 | 2.0 | +55 | 3.5 |

In all cases, reaction with succinic anhydride in pyridine results in an increase in cation-exchange capacity.

EXAMPLE 4

Variations on Example 2

The procedure described in Example 2(a) is used to convert succinylated sugar beet materials of Example 3 above to their Ca/Mg-free form. The cation exchange capacity of the dried products are given in Table 5.

TABLE 5

| Product Code # | Starting Material (Code #) | % Weight Change | Cation Exchange Capacity (meq/g) |
|---|---|---|---|
| 4B | 3B | −5 | 1.5 |
| 4C | 3C | −4 | 1.9 |
| 4E | 3E | −4 | 4.6 |

In all cases, acid treatment increases the cation-exchange capacity of the products.

EXAMPLE 5

Sorption Capacity of Sodium-Salt Form of Succinylated and Ca/Mg-Free Succinylated Sugar Beet Pulp The materials prepared in Examples 3 and 4 are converted to their sodium-salt form using the procedure described in Example 1(c). The cation-exchange capacity of the products is not substantially affected by this procedure. The absorbency of the products for synthetic urine are measured using the equilibrium-sorption test. The results are given in Table 6.

TABLE 6

| Product Code # | Starting Material (Code #) | % Weight Change | Absorbency (g/g) 1.0 PSI | Absorbency (g/g) 0.1 PSI | Bound Succinate (meq/g) |
|---|---|---|---|---|---|
| 5-(3A) | 3A | +1 | 7.0 | 13.3 | 0.0 |
| 5-(3B) | 3B | +1 | 8.7 | 17.9 | — |
| 5-(4B) | 4B | +1 | 10.0 | 20.2 | — |
| 5-(3C) | 3C | +1 | 9.4 | 18.5 | 1.0 |
| 5-(4C) | 4C | +1 | 11.4 | 21.8 | — |
| 5-(3D) | 3D | +3 | 11.1 | 19.1 | — |
| 5-(3E) | 3E | +6 | 11.8 | 17.4 | 2.3 |
| 5-(4E) | 4E | +8 | 12.2 | 17.9 | — |

All of the products with succinate substituents in their sodium salt form have absorbencies greater than that of the unreacted sugar beet pulp (Example 1a). No substantial increase in absorbency is found for the control sample of sugar beet pulp that receives identical treatment except for the absence of succinic anhydride (Example 5-(3A)). Samples that are acid treated to remove calcium and magnesium have higher absorbencies than comparable materials that are not acid treated.

Products #5-(3A), 5-(3C), and 5-(3E) are analyzed for bound succinate using the gas-chromatography procedure previously described. The results are given in Table 6. The values for bound succinate are in substantial agreement with the measured cation-exchange capacities.

EXAMPLE 6

Succinylation of Absorbent Sugar Beet Material with Succinic Anhydride in Pyridine (a) Preparation of Absorbent Sugar Beet Material An absorbent vegetable material is made from sugar beet pulp using the general procedure described in European Patent Application No. 84305279.6, by Rich, published Apr. 17, 1985, the disclosures of which are incorporated herein by reference. The resultant sugar beet material is 27.3 wt % pectin, with a degree of esterification of 36%, as determined by analysis for bound metals and methoxy content (Table 7). As a result of the pectin deesterification with sodium hydroxide using this procedure, 35 mole % of the pectin anhydrogalacturonate is present as the sodium salt.

TABLE 7

| Component | Percent Dry Weight | Meq/g | Mole % |
|---|---|---|---|
| Calcium | 0.62 | 0.31 | 22 |
| Magnesium | 0.12 | 0.10 | 7 |
| Sodium | 1.12 | 0.49 | 35 |
| Potassium | 0.01 | 0.00 | 0 |
| Methoxy (CH$_3$O) | 1.59 | 0.51 | 36 |
| Pectin | 27.3 | | |

The absorbency of this material for synthetic urine is 7.6 g/g and 13.6 g/g for confining weights of 1.0 psi and 0.1 psi, respectively. For distilled water, its absorbency is 8.5 g/g and 15 g/g for confining weights of 1.0 psi and 0.1 psi, respectively.

(b) Conversion of Absorbent Sugar Beet Material to Ca/Mg-Free Form 30 grams (26 grams dry weight) of the absorbent sugar beet material from part (a) above is dispersed in 1.1 liter deionized water. After stirring for one hour, 1.65 liters ethanol is added followed by 0.1 liters concentrated HCl.

After an additional 40 minutes of stirring, the dispersion is filtered. The filter cake is 2× resuspended in two liters 60/40 ethanol:water (60/40 V/V) and filtered. Water is removed using the procedure described in Example 1(b). 23 grams of dried product is obtained. The cation-exchange capacity of this material, as measured by titration, is 1.0 meq/g.

(c) Succinylation with Succinic Anhyride in Pyridine

Two 11 gram aliquots of the product from part (b) above are each dispersed in 800 mls of dry pyridine. Each is succinylated following the procedure described in Example 1(b), but with 9 grams of succinic anhydride. 28 grams of dried succinylated product is obtained, corresponding to a weight increase of 27%. The cation-exchange capacity of the product, as measured by titration, is 3.1 meq./g. The absorbency of the product for synthetic urine, as measured by the equilibrium-sorption test, is 5.5 g/g and 10.6 g/g for confining weights of 1.0 psi and 0.1 psi, respectively.

(d) Conversion of Succinylated Product to Sodium-Salt Form 1.55 grams of the succinylated product from part (c) above is converted to the sodium-salt form following a procedure analogous to the one described in Example 1(c). 1.50 grams of dried product is obtained. The absorbency of the product for synthetic urine, as measured by the equilibrium-sorption test, is 12.0 g/g and 21.1 g/g for confining weights of 1.0 psi and 0.1 psi, respectively. The absorbency of the product for distilled water, as measured by the equilibrium-sorption test, is 15.4 g/g and 23.0 g/g for confining weights of 1.0 psi and 0.1 psi, respectively. Thus, conversion of the succinylated product to its sodium-salt form substantially increases its absorbency for both synthetic urine and water. The product is also substantially more absorbent than the absorbent sugar-beet starting material of part (a) above. Also, the absorbency of the product is not substantially reduced when synthetic urine is used instead of distilled water as the absorbing fluid.

EXAMPLE 7

Succinylation of Absorbent Citrus Material with Succinic Anhydride in Pyridine (a) Preparation of Absorbent Citrus Material An absorbent citrus material is prepared as follows using the general procedures described in European Patent Application No. 84305279.6, by Rich, published Apr. 17, 1985, the disclosures of which are incorporated herein by reference. 129 grams of the albedo fraction of citrus peel obtained from California Valencia oranges are dispersed in an excess of distilled water. The dispersion is shredded for one minute in a blender. The dispersion is filtered and the filter cake redispersed in an excess of deionized water. This dispersion is adjusted to pH 10 and maintained at this pH for approximately 16 hours with 1N NaOH and a Radiometer pH-stat. The product is filtered and the filter cake redispersed in an excess of deionized water. Water is removed from the product following the procedure described in Example 1(a). 14 grams of dried product is obtained.

Absorbent citrus materials prepared using this procedure are typically 35% by weight pectin, with a degree of esterification of 5%, as determined by analysis for bound metals and methoxy content. Typical absorption capacities of this material for synthetic urine are 8 g/g and 11 g/g for confining weights of 1.0 psi and 0.1 psi, respectively.

(b) Succinylation of Absorbent Citrus Material and Conversion to Sodium-Salt Form 1.0 grams of the absorbent citrus material is dispersed in 150 mls of pyridine. This is succinylated following the procedure given in Example 1(b) except 1.0 gram of succinic anhydride is used. 1.23 grams of dried product is obtained, corresponding to a weight increase of 23%. The cation exchange capacity of the product, as measured by titration, is increased by 2.2 meq/g as a result of the reaction.

1.15 grams of the succinylated product is converted to the sodium-salt form using the procedure described in Example 1(c). 1.13 grams of dried product is obtained. The absorbency of the product for synthetic urine, as measured by the equilibrium-sorption test, is 10.5 g/g and 15.0 g/g for confining weights of 1.0 psi and 0.1 psi, respectively. These values are substantially greater than those of the absorbent citrus material prior to succinylation.

EXAMPLE 8

Phosphorylation of Sugar Beet Pulp with Phosphorous Oxychloride in Pyridine 73 grams of the never-dried sugar beet pulp described in Example 1(a) is dispersed in deionized water (1% solids) and shredded in a blender for one minute to reduce particle size. The resulting pulp dispersion is filtered, redispersed in deionized water, and adjusted to pH 7.5 by addition of 1N NaOH. The pulp dispersion is then filtered and the solids resuspended in water (1% solids) and refiltered to remove water-soluble components. Water is removed from the insoluble fraction by 2× exchange with ethanol, followed by 2× exchange with acetone, followed by drying. 15.6 grams of washed and dried sugar beet pulp material is obtained corresponding to a dry-weight yield of 85%.

1.0 gram of this washed and dried pulp is dispersed in 90 mls pyridine in a 3-neck 100 ml round-bottom flask. The dispersion is stirred for 30 minutes under anhydrous conditions. To this dispersion is added 0.2 mls of phosphorous oxychloride. The dispersion is stirred at ambient temperature for 5 minutes. Approximately 5 mls of distilled water is then added followed by filtration of the dispersion. The filter cake is 2× washed in deionized water by redispersion followed by filtration. Water is removed from the insoluble fraction by 2× exchange with ethanol, followed by 2× exchange with acetone, followed by drying. 1.13 grams of dried phosphorylated sugar-beet product is obtained, corresponding to a weight increase of 13%. The cation-exchange capacity of the product, as measured by titration, is 1.4 meq/g. 1.0 gram of the phosphorylated sugar beet pulp is dispersed in deionized water. The pH of the dispersion is adjusted to pH 8.5 with 1N NaOH and then maintained at this value for one hour using a Radiometer Recording Titration System. The dispersion is filtered, water-washed by 2× redispersion in deionized water, and dried using the method described above. 1.0 gram of dried phosphorylated sugar beet pulp in the sodium-salt form is obtained. The absorbency of the product for synthetic urine is measured using the equilibrium-sorption test. The absorption capacity is 11.2 g/g and 17.0 g/g for confining weights of 1.0 psi and 0.1 psi, respectively. This represents a substantial increase in absorbency compared to the unphosphorylated sugar beet pulp (Example 1(a)). Liquid sorption is very rapid.

EXAMPLE 9

Variation of Cation Exchange Capacity of Phosphorylated Sugar Beet Pulp

The phosphorylation procedure described in Example 8 is followed except for varying the amount of phosphorous oxychloride and reaction time. The % weight change and cation-exchange capacity, as measured by titration, are given in Table 8. The phosphorylated sugar beet products are converted to the sodium salt form using the procedure described in Example 8. The cation-exchange capacity of the products are not substantially affected by this procedure. Absorption capacities for synthetic urine are measured using the equilibrium-sorption test and are reported in Table 8. In all cases, absorbent capacities are greater than those of the unreacted sugar beet pulp (Example 1 (a)). Liquid sorption is very rapid for all samples. The sodium salt form of Samples #9C, 9E, and 9F are analyzed for bound phosphate using the procedure previously described.

TABLE 8

| Product Code # | Reaction | | | Cation Exchange Capacity (meq/g) | Absorbency (g/g) | | Bound Phosphate (meq/g) |
|---|---|---|---|---|---|---|---|
| | POCl$_3$ (ml) | Time (Min) | % Wt. Change | | 1.0 PSI | 0.1 PSI | |
| 9A | .06 | 5 | 0 | .6 | 8.1 | 16.4 | — |
| 9B | .12 | 5 | +3 | .9 | 9.4 | 18.5 | — |
| 9C | .20 | 40 | +16 | 1.5 | 10.8 | 15.4 | 1.5 |
| 9D | 1.00 | 5 | +25 | 2.4 | 9.8 | 14.2 | — |
| 9E | .50 | 40 | +33 | 3.4 | 9.2 | 12.5 | 2.3 |
| 9F | 2.00 | 40 | +40 | 4.6 | 8.5 | 11.3 | 2.6 |

EXAMPLE 10

Phosphorylation of Sugar Beet Pulp in Dimethylformamide Using Polyphosphoric Acid 0.9 gram of washed and dried sugar beet pulp (Example 1(a)) is added to a solution of 5.9 grams of polyphosphoric acid and 16.7 mls tributylamine in 40 mls dimethylformamide. The dispersion is heated to 120° C. and maintained at this temperature for 1.5 hours. After cooling to ambient temperature, the dispersion is filtered, washed 2× with ethanol, washed 2× with acetone, and dried. 1.0 grams of dried solids is obtained having a cation-exchange capacity, as measured by titration, of 1.4 meq/g.

0.9 grams of the phosphorylated product is converted to the sodium-salt form using the procedure described in Example 8. The absorbency of the product for synthetic urine is measured using the equilibrium-sorption test. The absorption capacity is 10.3 gms/gm and 17.5 g/g for confining weights of 1.0 psi and 0.1 psi, respectively. Liquid sorption is very rapid.

Bound phosphate in the sodium-salt form of the product is measured using the procedure previously described. The value for bound phosphate of 1.5 meq/g is in substantial agreement with the cation-exchange capacity of the product.

EXAMPLE 11

Preparation of Phosphorylated Sugar Beet 0.6 grams of washed and dried sugar beet pulp (Example 1(a)) is suspended in a mixture of 30 mls acetonitrile and 1.3 gram triethylamine. 0.24 grams of phosphorus oxychloride dissolved in 6 mls acetonitrile is added slowly to the stirred suspension of sugar beet pulp at room temperature. The reaction mixture is then heated to 55° C. and stirred at that temperature for 1 hr. After this time, the reaction mixture is cooled, water (1 ml) is added, and after stirring 10 minutes the mixture is filtered. The insoluble material is washed 2× with 50 mls of ethanol-water (85:15 v/v). The solid is then suspended in 30 ml ethanol/0.33N hydrochloric acid (85:15 v/v). After stirring 5 minutes, the suspension is filtered, and the residue is washed 4× with 50 mls ethanol, 4× with 50 ml ether, and dried in vacuo at room temperature to yield 0.63 grams of phosphorylated product. This material is converted to the sodium salt form using the procedure described in Example 1(c).

The absorbency for synthetic urine of this product, and the products from two other phosphorylation reactions performed as described above using acetonitrile as the solvent with different ratios of phosphorous oxychloride to pulp, is measured using the equilibrium-sorption test. The absorption capacity of these products is given in Table 9.

Phosphorylation reactions are also performed as described above using acetone as the solvent. The absorbency of products from these reactions for synthetic urine, as measured by the equilibrium-sorption test, is given in Table 10.

TABLE 9

| | Phosphorylation in Acetonitrile | | |
|---|---|---|---|
| POCl₃ | Cation Exchange Capacity | Absorbency (g/g) | |
| (ml/g pulp) | (meq/g) | 1 PSI | 0.1 PSI |
| 0.4 | 1.1 | 11.3 | 12.0 |
| 0.8 | 1.7 | 10.3 | 14.2 |
| 1.2 | 2.6 | 8.5 | 10.9 |

TABLE 10

| | Phosphorylation in Acetone | | |
|---|---|---|---|
| POCl₃ | Cation Exchange Capacity | Absorbency (g/g) | |
| (ml/g pulp) | (meq/g) | 1 PSI | 0.1 PSI |
| 0.2 | 0.7 | 9.3 | 16.6 |
| 0.4 | 1.0 | 10.5 | 17.8 |
| 0.8 | 1.7 | 10.1 | 13.5 |
| 1.2 | 2.4 | 9.7 | 12.3 |

EXAMPLE 12

Succinylation in Acetone

A mixture of 0.5 g washed and dried sugar beet pulp (Example 1 (a)), 0.5 g triethylamine, 0.5 g succinic anhydride, and 25 mls acetone is refluxed for 17 hrs. The cooled reaction mixture is filtered and the succinylated product is washed 2× with 50 ml ethanol-water (85:15 v/v) followed by soaking in 30 ml ethanol/0.33N hydrochloric acid (85:15 v/v). After a few minutes the suspension is filtered and the solid is washed successively 4× with 50 ml ethanol, 4× with 50 ml ether, and dried in vacuo to yield 0.8 g of succinylated product. This material is converted to the sodium salt form using the procedure described in Example 1(c). The absorbency for synthetic urine of this product, and the product of another succinylation reaction performed as above using a different ratio of succinic anhydride to pulp, is measured using the equilibrium-sorption test. The absorption capacity of these products is given in Table 11.

TABLE 11

| | Succinylation in Acetone | | |
|---|---|---|---|
| Succinic Anhydride | Cation Exchange Capacity | Absorbency (g/g) | |
| (g/g pulp) | (meq/g) | 1 PSI | 0.1 PSI |
| 1 | 2.3 | 11.1 | 18.0 |

TABLE 11-continued

| | Succinylation in Acetone | | |
|---|---|---|---|
| Succinic Anhydride | Cation Exchange Capacity | Absorbency (g/g) | |
| (g/g pulp) | (meq/g) | 1 PSI | 0.1 PSI |
| 2 | 2.5 | 10.3 | 15.9 |

EXAMPLE 13

Succinylation in Acetonitrile

Three succinylation reactions are carried out as described in Example 12 except that boiling acetonitrile is used in place of acetone, an equivalent amount of pyridine is used instead of triethylamine, and the reaction time is varied. The absorption capacity of these products, as well as the reaction times, are given in Table 12.

TABLE 12

| | Succinylation in Acetonitrile | | | |
|---|---|---|---|---|
| Succinic Anhydride | Reaction Time | Cation Exchange Capacity | Absorbency (g/g) | |
| (g/g pulp) | (hrs) | (meq/g) | 1 PSI | 0.1 PSI |
| 2 | 3 | 2.9 | 11.3 | 17.8 |
| 2 | 6 | 2.3 | 9.9 | 16.9 |
| 2 | 18 | — | 7.3 | 11.7 |

EXAMPLE 14

Maleylation in Acetone

The treatment of washed and dried sugar beet pulp (Example 1(a)) with maleic anhydride and triethylamine in acetone solvent is carried out as described for the succinylation reactions in Example 12. The absorption capacity of these products, as well as reaction times, are given in Table 13.

TABLE 13

| | Maleylation in Acetone | | | |
|---|---|---|---|---|
| Maleic Anhydride | Reaction Time | Cation Exchange Capacity | Absorbency (g/g) | |
| (g/g pulp) | (hrs) | (meq/g) | 1 PSI | 0.1 PSI |
| 0.5 | 5 | 2.2 | 10.5 | 19.1 |
| 1.0 | 5 | 2.7 | 10.9 | 18.6 |
| 1.0 | 17 | 2.4 | 9.7 | 15.8 |
| 2.0 | 17 | 2.6 | 9.3 | 14.1 |

EXAMPLE 15

Succinylation of Sugar Beet Pulp (a) Raw Materials 660 g of never-dried sugar beet pulp cossettes (23.9% solids) is dispersed in distilled water (2% solids) and shredded in a Waring commercial blender for 3 minutes to reduce particle size. The slurry is filtered, redispersed in distilled water and adjusted to pH=7.5 for 1 hr. by the addition of 1N NaOH. This slurry is then filtered and redispersed 2× in distilled water (1% solids) to remove water-soluble components. Following washing 2× with ethanol:methanol (95:5, 1% solids), and 2× with acetone (1% solids) the pulp is dried under vacuum overnight. 140 grams of dry pulp is obtained (88.6% yield).

(b) Succinylation of Sugar Beet Pulp with Succinic Anhydride in Pyridine 140 grams of the above washed and dried pulp is dispersed in 7 liters pyridine (2% solids) in a 12 liter 3-neck round-bottom flask. The dispersion is stirred under nitrogen 20 minutes at ambient temperature. To this dispersion is then added 140 grams of succinic anhydride. This dispersion is stirred an additional 30 minutes at ambient temperature to dissolve the succinic anhydride, then is heated to 80° C. and stirred at that temperature for 2 hrs. After this time the reaction mixture is cooled to room temperature and filtered. The solids are redispersed 2× in ethanol:methanol (95:5, 2% solids) to remove pyridine and unreacted succinic anhydride, and 1× in distilled water (2% solids). The wet filter cake is redispersed in distilled water:ethanol:methanol (36:61:3; 1% solids), 280 ml of concentrated HCl is added to this well stirred slurry, and then the slurry is filtered after 3 minutes. The pulp is washed 2× with distilled water:ethanol:methanol (40:57:3; 2% solids), dispersed in distilled water (0.5% solids), and then adjusted to pH=8.5 with 1N NaOH and maintained at this pH for 4.5 hours using a Radiometer recording titration system and pH stat. The dispersion is filtered, and then washed 2× with distilled water (2% solids), 2× with ethanol:methanol (95:5; 2% solids), and 2× with acetone (2% solids). Drying under vacuum yields 158 grams of succinylated sugar beet pulp. The absorbency of this product for synthetic urine, as measured by the equilibrium-sorption test, is 11.4 g/g and 15 g/g for confining weights of 1.0 psi and 0.1 psi, respectively.

EXAMPLE 16

Vegetable Absorbent Material and Conventional Absorbent Material Structures

The sugar beet-derived vegetable material produced in Example 15 is mixed with Foley fluff (southern softwood kraft), in a ratio by weight of Foley fluff/vegetable material of 1:1, using conventional air laying equipment and densified to form a web with a density of about 0.25 g/cm³. An absorbent structure of the same materials as above in a ratio of 65 Foley fluff:35 vegetable material, is made using the same process as above (density approximately 0.25 g/cm³).

Examples of other absorbent structures of the present invention are:

|  | A | B | C |
|---|---|---|---|
| Vegetable material (wt. %) | 80 | 75 | 10 |
| Kraft pulp fibers (wt. %) | 20 | 25 | 90 |

The resulting structures possess excellent absorbent properties and are suitable for use in e.g., diapers and sanitary napkins.

EXAMPLE 17

Vegetable Absorbent Material and Conventional Absorbent Material Structures

The sugar beet-derived vegetable absorbent material of the present invention in its salt form is mixed, using conventional air-laying equipment to form webs, with particles of a polyacrylate grafted starch water-insoluble hydrogel ("Sanwet 1M 1000", from Sanyo Chemical Industries, Ltd., Japan) in the following ratios:

|  | A | B | C |
|---|---|---|---|
| Vegetable absorbent material (wt. %) | 50 | 75 | 95 |
| Water-insoluble hydrogel (wt. %) | 50 | 25 | 5 |

The resulting structures possess excellent absorbent properties and are suitable for use in e.g., diapers and sanitary napkins.

EXAMPLE 18

Vegetable Absorbent Material and Conventional Absorbent Material Structures

The citrus pulp-derived vegetable absorbent material of the present invention in its salt form is mixed, using conventional air-laying equipment to form webs, with cellulose pulp fibers and particles of a polyacrylate grafted starch water-insoluble hydrogel ("Sanwet 1M 1000", from Sanyo Chemical Industries, Ltd., Japan) in the following ratios:

|  | A | B | C | D |
|---|---|---|---|---|
| Vegetable Absorbent Material (wt. %) | 50 | 20 | 35 | 10 |
| Kraft pulp fibers (wt. %) | 30 | 30 | 45 | 80 |
| Water-insoluble hydrogel (wt. %) | 20 | 50 | 20 | 10 |

The resulting structures possess excellent absorbent properties and are suitable for use in, e.g., diapers and sanitary napkins.

EXAMPLE 19

Densified Absorbent Structures

The absorbent structure "A" of Example 16 is compressed using a conventional pressing device to densify the structure to 0.15 g/cm³.

Examples of other densified structures include: structure "B" of Example 16, densified to 0.2 g/cm³; structure "C" of Example 16, densified to 0.1 g/cm³; structure "A" of Example 17, densified to 0.4 g/cm³; structure "B" of Example 17, densified to 0.3 g/cm³; structure "C" of Example 17, densified to 0.2 g/cm³; and structures "A", "B", "C" and "D" of Example 18, densified to 0.2 g/cm³.

The resulting structures possess excellent absorbent properties and low bulk, and are suitable for use in, e.g., diapers and sanitary napkins.

EXAMPLE 20

Absorbent Structure Containing Additional Components

A polyester-reinforced absorbent structure is prepared as follows:

2 g. of 6 denier polyester fiber, fiber length about 4 in. (about 10 cm), is carded and formed into an unbonded web, and then placed on a wire screen which is covered with a tissue. A mixture (4:1 by weight) of sugar beet-derived vegetable absorbent material of the present invention in its salt form and particles of a polyacrylate grafted starch water-insoluble hydrogel ("Sanwet 1M 1000", from Sanyo Chemical Industries, Ltd., Japan) is poured over the polyester fiber web, and forced into the web by reducing the air pressure under the wire screen. The resulting structure is compressed in a flat hydraulic press to a density of 0.2 g/cm³. The absorbent structure with this polyester fiber reinforcement possesses excellent absorbent and strength properties, and is suitable for use, in e.g., diapers and sanitary napkins.

EXAMPLE 21

Diapers Employing an Absorbent Structure Pursuant to this Invention

Disposable diapers utilizing absorbent structures of the present invention are prepared as follows:

The absorbent structure prepared as in Example 19 is enveloped in wet strength tissue paper having a basis weight of about 12 pounds per 3,000 square feet (about 20 g/m$^2$), a dry tensile strength of about 700 g/inch (about 275 g/cm) in the machine direction and about 300 g/inch (about 120 g/cm) in the cross machine direction.

The enveloped pad is glued onto a 7 in. ×11 in. (about 18 cm×28 cm) backsheet of embossed polyethylene film having a melt index of about 3 and a density of about 0.92 g/cm$^3$. The ends of the backsheet are folded over the enveloped pad and attached with glue. Finally, the absorbent pad is covered with a topsheet of hydrophobic but water and urine pervious material. (Webline No. F 6211 from Kendall Co. of Walpole, Mass., comprised of a non-woven rayon bonded with an acrylic latex). The resulting absorbent structure is useful as a diaper and has excellent properties of absorption and containment of urine.

Similarly, diapers are prepared using citrus pulp-derived (or other vegetable material-derived) absorbent vegetable material of the present invention.

EXAMPLE 22

Sanitary Napkins Employing an Absorbent Structure Pursuant to this Invention

Sanitary napkins utilizing absorbent structures of the present invention are prepared as follows:

An absorbent structure, prepared as in Example 16, is calendered to a density of about 0.4 g/cm$^3$ as measured under a confining pressure of 0.1 PSI (about 7×10$^3$ N/m$^2$). The web is cut into a pad of 8 in.×2 in. (about 20 cm×5 cm) with tapered ends. On top of this pad is placed a second pad (rectangular) of 5 in.×2 in. (about 13 cm×5 cm). The combined pad structure is placed against a waterproof backing sheet (8 in.×2 in. (about 20 cm×5 cm) tapered) of embossed hard polyethylene having an embossed caliper of 1.5 mils. The structure is covered with a top sheet of non-woven, 3 denier needle punched polyester fabric having a density of about 0.03 g/cm$^3$ and a caliper of about 2.3 mm. The thus covered structure is placed on a 9 in.×3 in. (about 23 cm×7.5 cm) bottom sheet of hydrophobic, spinbonded non-woven polyester having a measured weight of about 15 g/m$^2$. The bottom sheet is prefolded upwardly by means of heat and pressure which bonds the superposed sheets together. The resulting absorbent structure is useful as a sanitary napkin and has excellent properties of absorption and containment of menses exudate.

Similarly, sanitary napkins are prepared using citrus-pulp-derived (or other vegetable material-derived) absorbent vegetable material of the present invention.

What is claimed is:

1. A vegetable material derived from a pectin-containing vegetable starting-material selected from the group consisting of sugar beet pulp, citrus pulp, apple pulp, apricot pulp, watermelon rinds, or combinations thereof and comprising:
    (1) from about 5% to about 60% pectin;
    (2) from about 5% to about 60% of substituents containing cation exchange groups which have been incorporated into said pectin-containing vegetable starting-material without separation or separate addition of pectin;
    (3) from about 0.5 meq/g to about 6 meq/g of cation exchange groups; and
    (4) from about 20% to about 85% of non-pectin vegetable material.

2. A vegetable material according to claim 1 in which the non-pectin material constitutes:
    (1) from about 80% to about 100% of a material selected from the group consisting of cellulose, hemicellulose, lignin, and mixtures thereof;
    (2) from about 0% to about 5% chloroform soluble lipids; and
    (3) from about 0% to about 15% non-lipid organic materials extractable in a mixture of chloroform, methanol and water, said mixture having a volume ratio chloroform:methanol:water of 20:4:1.

3. A vegetable material according to claim 1 comprising from about 5% to about 35% of substituents containing cation exchange groups which have been incorporated into the vegetable material.

4. A vegetable material according to claim 1 comprising from about 1.0 meq/g to about 3.5 meq/g of cation exchange groups.

5. A vegetable material according to claim 1 comprising from about 5% to about 35% of substituents containing cation exchange groups which have been incorporated into the vegetable material, and from about 1.0 meq/g to about 3.5 meq/g of cation exchange groups.

6. A vegetable material according to claim 1 derived from sugar beet pulp.

7. A vegetable material according to claim 1 derived from citrus pulp.

8. A vegetable material according to claim 1 derived from a mixture of (1) from about 1% to about 99% of sugar beet pulp and (2) from about 1% to about 99% of citrus pulp.

9. A vegetable material according to claim 1 in which the substituents containing cation exchange groups are polyprotic acids.

10. A vegetable material according to claim 9 in which the polyprotic acids are organic dicarboxylic acids.

11. A vegetable material according to claim 10 in which the organic dicarboxylic acids are succinic acids.

12. A vegetable material according to claim 10 in which the organic dicarboxylic acids are maleic acids.

13. A vegetable material according to claim 9 in which the polyprotic acids are phosphates.

14. A vegetable material according to claim 1 in its acid form.

15. A vegetable material according to claim 1 in its salt form.

16. A vegetable material according to claim 15 in its salt form selected from sodium salts, potassium salts, and mixtures thereof.

17. A process for producing absorbent vegetable materials having from about 0.5 meq/g to about 6 meq/g of cation exchange groups, starting with vegetable materials inherently containing from about 15% to about 60% pectin, comprising:
    (1) performing the steps, one or more times, in any order, of
        (a) incorporating into the vegetable material substituents containing cation exchange groups to the extent of from about 0.5 meq to about 6.0 meq of cation exchange groups per gram of substituent-containing vegetable material; and (2) adjusting the pH of the vegetable material to the desired pH using a base or acid containing an exchangeable cation.

18. A process for producing absorbent vegetable materials according to claim 17 in which the vegetable starting material is selected from the group consisting of sugar beet pulp, citrus pulp, apple pulp, apricot pulp, watermelon rinds, or combinations thereof.

19. A process for producing absorbent vegetable materials according to claim 18 in which the vegetable starting material is sugar beet pulp.

20. A process for producing abosrbent vegetable materials according to claim 18 in which the vegetable starting material is citrus pulp.

21. A process for producing absorbent vegetable materials according to claim 18 in which the vegetable starting material is a mixture of (1) from about 1% to about 99% of sugar beet pulp, and (2) from about 1% to about 99% of citrus pulp.

22. A process for producing absorbent vegetable materials according to claim 17 wherein step 1(a) constitutes reacting the vegetable material with polyprotic acids, or the anhydrides or acid halides of polyprotic acids.

23. A process according to claim 22 in which the polyprotic acids are selected from the group consisting of organic dicarboxylic acid anhydrides, organic dicarboxylic acid halides, phosphorous oxychloride, and polyphosphoric acid.

24. A process according to claim 23 in which the organic dicarboxylic acid anhydrides are succinic anhydride or maleic anhydride.

25. A process for producing absorbent vegetable materials according to claim 17 in which, in step (2), the vegetable material is adjusted to a pH below about 5.

26. A process for producing absorbent vegetable materials according to claim 17 in which, in step (2), the vegetable material is adjusted to a pH of from about 5 to about 10.

27. A process for producing absorbent vegetable materials according to claim 26 in which, in step (2), the vegetable material is adjusted to pH from about 5 to about 10 using NaOH, KOH, or HCl.

28. A process according to claim 17 in which, in step 1(a), the vegetable material is reacted with polyprotic acids, or the anhydrides or acid halides of polyprotic acids, in a solvent selected from the group consisting of pyridine, acetone with a trialkylamine catalyst, dimethylformamide with a trialkylamine catalyst, and acetonitrile with a trialkylamine catalyst.

29. A process according to claim 28 in which the polyprotic acid is selected from the group consisting of succinic anhydride, maleic anhydride, phosphorous oxychloride, and polyphosphoric acid.

30. A process according to claim 29 in which the trialkylamine catalyst is triethylamine or tributylamine.

31. A process according to claim 17, starting with sugar beet pulp, citrus pulp, or mixtures thereof, comprising:
(1) reacting the vegetable material with a polyprotic acid selected from the group consisting of organic dicarboxylic acid anhydrides, organic dicarboxylic acid halides, phosphorous oxychloride, and polyphosphoric acid, in a solvent selected from the group consisting of pyridine, acetone with a trialkylamine catalyst, dimethylformamide with a trialkylamine catalyst, and acetonitrile with a trialkylamine catalyst; followed by,
(2) adjusting the pH of the vegetable material to from about 5 to about 10 using KOH, NaOH, or HCl.

32. A process for producing absorbent vegetable materials having from about 0.5 meq/g to about 6 meq/g of cation exchange groups, starting with vegetable materials inherently containing from about 15% to about 60% pectin, comprising:
(1) performing the steps, one or more times, in any order, of
(a) incorporating into the vegetable material substituents containing cation exchange groups to the extent of from about 0.5 meq to about 6.0 meq of cation exchange groups per gram of substituent-containing vegetable material; and
(b) modifying the vegetable material to increase its cation exchange capacity; and,
(2) adjusting the pH of the vegetable material to the desired pH using a base or acid containing an exchangeable cation.

33. A process according to claim 32 in which the vegetable material is modified to increase its cation exchange capacity, in step 1(b), by a process selected from the group consisting of soaking the vegetable material in a dilute HCl solution, soaking the vegetable material in about a 1M aqueous NaCl solution, and alkaline treatment of the vegetable material at pH of from about 8 to about 11 to reduce the degree of esterification in the pectin.

34. A process according to claim 32, starting wih sugar beet pulp, citrus pulp, or mixtures thereof, comprising:
(1) reacting the vegetable material with a polyprotic acid selected from the group consisting of organic dicarboxylic acid anhydrides, organic dicarboxylic acid halides, phosphorous oxychloride, and polyphosphoric acid, in a solvent selected from the group consisting of pyridine, acetone with a trialkylamine catalyst, dimethylformamide with a trialkylamine catalyst, and acetonitrile with a trialkylamine catalyst; followed by,
(2) modifying the cation exchange capacity of the vegetable material by a process selected from the group consisting of soaking the vegetable material in a dilute HCl solution, soaking the vegetable material in about a 1M aqueous NaCl solution at about neutral pH followed by washing the vegetable material with about a 1M aqueous NaCl solution, and alkaline treatment of the vegetable material at pH of from about 8 to about 11 to reduce the degree of esterification in the pectin; followed by,
(3) adjusting the pH of the vegetable material to from about 5 to about 10 using KOH, NaOH, or HCl.

35. A process according to claim 32, starting with sugar beet pulp, citrus pulp, or mixtues thereof, comprising:
(1) modifying the cation exchange capacity of the vegetable material by a process selected from the group consisting of soaking the vegetable material in a dilute HCl solution, soaking the vegetable material in about a 1M aqueous NaCl solution at about neutral pH followed by washing the vegetable material with about a 1M aqueous NaCl solution, and alkaline treatment of the vegetable material at pH of from about 8 to about 11 to reduce the degree of esterification in the pectin; followed by, (2) reacting the vegetable material with a polyprotic acid selected from the group consisting of organic dicarboxylic acid anhydrides, organic dicarboxylic acid halides, phosphorous oxychloride, and polyphosphoric acid, in a solvent selected from the group consisting of pyridine, acetone with a trialkylamine catalyst, dimethylformamide with a trialkylamine catalyst, and acetonitrile with a trialkylamine catalyst; followed by, (3) adjusting the pH of the vegetable material to from about 5 to about 10 using KOH, NaOH, or HCl.

36. In a process for preparing vegetable absorbent materials based on pectin-containing vegetable starting-material, the improvement which comprises at least one step consisting of reacting, with a polyprotic acid reactant, the components of a pectin-containing vegetable starting-material having a pectin content of from about 15% to about 60% and consisting of sugar beet pulp, citrus pulp or a mixture thereof, to form a vegetable material containing, per gram, from about 0.5 meq to about 6.0 meq of cation exchange groups; provided that in said process, said pectin is not removed from said components for the purpose of separate reaction.

37. A product produced by a process according to claim 36, wherein said polyprotic acid reactant is selected from the group consisting of succinic anhydride, maleic anhydride, phosphorus oxychloride and polyphosphoric acid.

38. The product produced by the process according to claim 17.

39. The product produced by the process according to claim 31.

40. The product produced by the process according to claim 32.

41. The product produced by the process according to claim 34.

42. The product produced by the process according to claim 35.

43. A vegetable absorbent material, further characterized in that it is vegetable material, produced by the process of claim 36 and having said cation exchange groups in monovalent salt form.

44. An absorbent structure comprising
(1) from about 1% to about 99% of an absorbent vegetable material according to claim 15; and
(2) from 1% to about 99% of other absorbent material.

45. An absorbent structure comprising
(1) from about 1% to about 99% of an absorbent vegetable material according to claim 38; and
(2) from 1% to about 99% of other absorbent material.

46. An absorbent structure comprising
(1) from about 1% to about 99% of an absorbent vegetable material according to claim 39; and
(2) from 1% to about 99% of other absorbent material.

47. An absorbent structure comprising
(1) from about 1% to about 99% of an absorbent vegetable material according to claim 41; and
(2) from 1% to about 99% of other absorbent material.

48. An absorbent structure comprising
(1) from about 1% to about 99% of an absorbent vegetable material according to claim 42; and
(2) from 1% to about 99% of other absorbent material.

49. A disposable absorbent product comprising:
(1) a hydrophobic top sheet;
(2) a liquid impervious backing sheet; and
(3) an absorbent core of vegetable material according to claim 15, said core being placed between the backing sheet and the top sheet.

50. A disposable absorbent product comprising
(1) a hydrophobic top sheet;
(2) a liquid impervious backing sheet; and
(3) an absorbent core of vegetable material according to claim 38, said core being placed between the backing sheet and the top sheet.

51. A disposable absorbent product comprising:
(1) a hydrophobic top sheet;
(2) a liquid impervious backing sheet; and
(3) an absorbent core of vegetable material according to claim 39, said core being placed between the backing sheet and the top sheet.

52. A disposable absorbent product comprising:
(1) a hydrophobic top sheet;
(2) a liquid impervious backing sheet; and
(3) an absorbent core of vegetable material according to claim 41, said core being placed between the backing sheet and the top sheet.

53. A disposable absorbent product comprising:
(1) a hydrophobic top sheet;
(2) a liquid impervious backing sheet; and
(3) an absorbent core of a vegetable material according to claim 42, said core being placed between the backing sheet and the top sheet.

54. A disposable absorbent product comprising:
(1) a hydrophobic top sheet;
(2) a liquid impervious backing sheet; and
(3) an absorbent core of an absorbent structure according to claim 40, said core being placed between the backing sheet and the top sheet.

55. A disposable absorbent product comprising:
(1) a hydrophobic top sheet;
(2) a liquid impervious backing sheet; and
(3) an absorbent core of an absorbent structure according to claim 45, said core being placed between the backing sheet and the top sheet.

56. A disposable absorbent product comprising:
(1) a hydrophobic top sheet;
(2) a liquid impervious backing sheet; and
(3) an absorbent core of an absorbent structure according to claim 46, said core being placed between the backing sheet and the top sheet.

57. A disposable absorbent product comprising:
(1) a hydrophobic top sheet;
(2) a liquid impervious backing sheet; and
(3) an absorbent core of an absorbent structure according to claim 47, said core being placed between the backing sheet and the top sheet.

58. A disposable absorbent product comprising:
(1) a hydrophobic top sheet;
(2) a liquid impervious backing sheet; and
(3) an absorbent core of an absorbent structure according to claim 48, said core being placed between the backing sheet and the top sheet.

* * * * *